(12) United States Patent
Hansen et al.

(10) Patent No.: US 8,634,914 B2
(45) Date of Patent: Jan. 21, 2014

(54) PACEMAKER EVENT QUEUE TO CONTROL DEVICE PROCESSOR OPERATING POWER

(75) Inventors: Daniel L. Hansen, Castle Rock, CO (US); Robert M. Ecker, Lino Lakes, MN (US); Paul R. Solheim, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/359,513

(22) Filed: Jan. 27, 2012

(65) Prior Publication Data
US 2013/0198531 A1    Aug. 1, 2013

(51) Int. Cl.
*A61N 1/362*    (2006.01)

(52) U.S. Cl.
USPC .................................. 607/16; 607/9

(58) Field of Classification Search
None
See application file for complete search history.

(56) References Cited

U.S. PATENT DOCUMENTS

| | | | |
|---|---|---|---|
| 4,381,010 A | | 4/1983 | Thompson et al. |
| 4,554,920 A | | 11/1985 | Baker, Jr. et al. |
| 4,823,292 A | * | 4/1989 | Hillion .......................... 713/321 |
| 6,141,583 A | | 10/2000 | Pape et al. |
| 6,185,454 B1 | | 2/2001 | Thompson |
| 6,269,412 B1 | | 7/2001 | Liu et al. |
| 6,400,985 B1 | | 6/2002 | Amely-Velez |
| 6,442,428 B1 | | 8/2002 | Shankar et al. |
| 6,496,729 B2 | | 12/2002 | Thompson |
| 6,804,631 B2 | | 10/2004 | Kelley et al. |
| 7,085,952 B2 | | 8/2006 | Huelskamp |
| 7,123,958 B1 | | 10/2006 | Wong |
| 7,801,615 B2 | | 9/2010 | Meadows et al. |
| 7,827,011 B2 | | 11/2010 | DeVaul et al. |
| 7,899,522 B1 | | 3/2011 | Koh et al. |
| 2002/0144099 A1 | | 10/2002 | Muro, Jr. et al. |
| 2007/0038250 A1 | | 2/2007 | He et al. |
| 2007/0208261 A1 | | 9/2007 | Maniak et al. |
| 2010/0312188 A1 | | 12/2010 | Robertson et al. |
| 2011/0125095 A1 | * | 5/2011 | Lebel et al. .................... 604/151 |

FOREIGN PATENT DOCUMENTS

| | | |
|---|---|---|
| WO | 0162142 A2 | 8/2001 |
| WO | 2009005950 A2 | 1/2009 |

OTHER PUBLICATIONS (PCT/US2012/064017) PCT Notification of Transmittal of the International Search Report and the Written Opinion of the International Searching Authority, Mailed Feb. 8, 2013, 12 pages.

\* cited by examiner

*Primary Examiner* — Carl H Layno
*Assistant Examiner* — Ankit Tejani
(74) *Attorney, Agent, or Firm* — Evans M. Mburu

(57) ABSTRACT

In the present disclosure, conservation of an implantable medical device power supply of is facilitated by controlling the power consumption of the device's processing component. The power supplied to the processing component is controlled to enable processing of received events as a function of predetermined criteria rather than the actual occurrence of the events which is frequent, but irregular. Accordingly, the need for the processing component to start and stop (and thereby be fully powered on each start) with receipt of each event is obviated thereby maintaining the power consumption of the processing component and increasing longevity of the device. Event data associated with received events is stored in an event queue and subsequently retrieved and transmitted for processing based on predetermined criteria. The power supplied during an idle state of the processing component may be reduced in relation to the power supplied during a wake up state.

9 Claims, 8 Drawing Sheets

PACEMAKER EVENT QUEUE TO CONTROL DEVICE PROCESSOR OPERATING POWER

FIELD

This disclosure relates generally to implantable medical devices and, more particularly, to control of power consumption.

BACKGROUND

The technology explosion in the implantable medical device (IMD) industry has resulted in many new and innovative devices and methods for analyzing the health of a patient and/or providing therapies to improve quality of life. IMDs include pacemakers, implantable cardioverter-defibrillators (ICDs), neural stimulators, drug administering devices, monitors, etc. State-of-the-art IMDs are capable of performing significantly more complex tasks and are vastly more sophisticated and complex than earlier IMDs and their therapeutic benefits have been well established.

There are many IMDs that provide data acquisition of important physiologic data from a human body, e.g. cardiac IMDs that acquire cardiac data. Such cardiac IMDs include implantable heart monitors that only monitor and acquire cardiac data and therapy delivery IMDs that both acquire cardiac data and provide appropriate therapies, such as single chamber, dual chamber, and bi-ventricular pacemakers, ICDs that typically incorporate pacing systems for treating bradycardia and tachyarrhythmias, and cardiomyostimulators. The therapy delivery cardiac IMDs comprise an implantable pulse generator (IPG) that is coupled with one or more electrical medical lead bearing electrodes for sensing the inter-cardiac or remote electrogram (EGM) and/or delivering pacing pulses or cardioversion/defibrillation shocks to the heart.

Cardiac IMDs and other IMDs can include the capability of communicating, through radio frequency telemetry transmissions, with external medical devices to enable programming and interrogation of the IMD through downlink telemetry transmissions and to enable uplink telemetry transmissions of data from the IMD to the external medical device.

Cardiac IPGs and monitors as well as other IMDs are powered by an internal power source, typically one or more batteries, that serves a variety of functions, including, but not limited to, supplying power to electronic components and circuitry and charging high voltage capacitors that are discharged through medical electrical leads into the heart to regulate heart rhythms. The functional sophistication and complexity of the IMD operating systems powered by the battery have increased over the years. Battery powered IMDs must be replaced when the battery become depleted, and therefore conserving battery power is important to maintain or prolong the life of the IMD. Therefore, much effort has been devoted to increasing conservation of battery resources.

The IMD electronics include a microcontroller that is operated in accordance with stored software, or firmware, or a combination of both. Generally, the microcontroller is programmed to respond to events as they are detected by other discrete components of the IMD electronics. With each response to the events, the depletion of the battery is increased. What is needed are power conservation techniques that optimize the operation of the microcontroller as a function of responding to the events.

SUMMARY

Generally, the disclosure enables optimization of power consumption by an implantable medical device ("IMD"). The disclosure may be embodied in an IMD of the type performing monitoring of a physiologic state and/or therapy delivery under the control of a control unit such for example as a microcontroller or microprocessor. In order to extend the life of the IMD, it is generally desired to reduce the power consumption of the control unit. One such reduction can be achieved by providing power to the control unit only during a processing operation and withholding the supply of power or substantially reducing the delivered power level during an idle state.

Accordingly, one embodiment of the disclosure includes providing power at a first power level to a processor during a first state and providing power at a second power level to the processor in response to a control signal. The control signal may be generated based on predetermined criteria to enable processing of data by the processor.

In an embodiment, an event is detected by sense circuitry of the IMD and data associated with the event is stored in a memory location such as an event queue. The stored data may include the pertinent event information, a time stamp and a classification of the event. The events may be stored in any desired pattern and retrieved in any preferred manner such, for example, as first-in first-out, first-in last-out, or randomly.

In an embodiment, a head pointer may be utilized to track the events stored in the queue, and a tail pointer may track the events transferred to the processor to be processed. An interrupt signal may be generated in response to predetermined criteria to initialize transfer of the event data to the processing component. Examples of such criteria may include the number of events between tail pointer and head pointer exceeding a programmed count, receipt of an event identified in a given category, or storage of events within a given time window.

In yet another embodiment, a first clock signal is provided to the processor during the idle state and a second clock signal is provided responsive to the interrupt signal. In an example, the first clock signal may be significantly slower in comparison to the second clock signal.

Accordingly, the techniques of the present disclosure provide the flexibility to control how frequently the control unit starts and stops running, based on the need for processing of event information and as such facilitate power-savings of the battery resources of an IMD.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION OF THE DRAWINGS

Implantable medical devices ("IMD") include electronics having a combination of ultra-low power micro-electronic circuits and a low-power microcontroller to obtain the desired combination of flexibility and longevity. The microcontroller provides feature flexibility and the microelectronics keep the power consumption at a minimum.

Within the IMD, there are many discrete processes involving collecting, storing, and presenting physiologic trends of a patient, as well as in delivering therapies (e.g., a cardiac therapy). The battery located within the IMD provides the power necessary for performing such operations. The components utilized for performing each of the various operations draws a threshold amount of power (power level) from the finite source battery to perform its intended operation. Therefore, conserving battery power can provide for longer, uninterrupted operation of the IMD. Many IMDs are operated in what will hereafter be referred to as an "idle state," that is to say that a certain portion of circuitry in the IMD is shut down or a minimal amount of current is supplied thereto, in response to that portion not being immediately needed, in order to conserve power.

The inventors of the present disclosure have developed a scheme for controlling the operation of the IMD between the idle state and a wake up state, which is when a normal current level is provided to the microcontroller. In general, it should be understood that the normal current level of a given microcontroller is determined by the manufacturer of the microcontroller and the level may vary from manufacturer to manufacturer. However, for purposes of this disclosure, it is believed sufficient to note that the microcontroller will be provided with power supply at a first power level in which the microcontroller essentially receives little to no current and is not executing code, and/or the microcontroller is supplied with power at a second power level so as to perform a desired function such as a processing operation.

Figure 1:
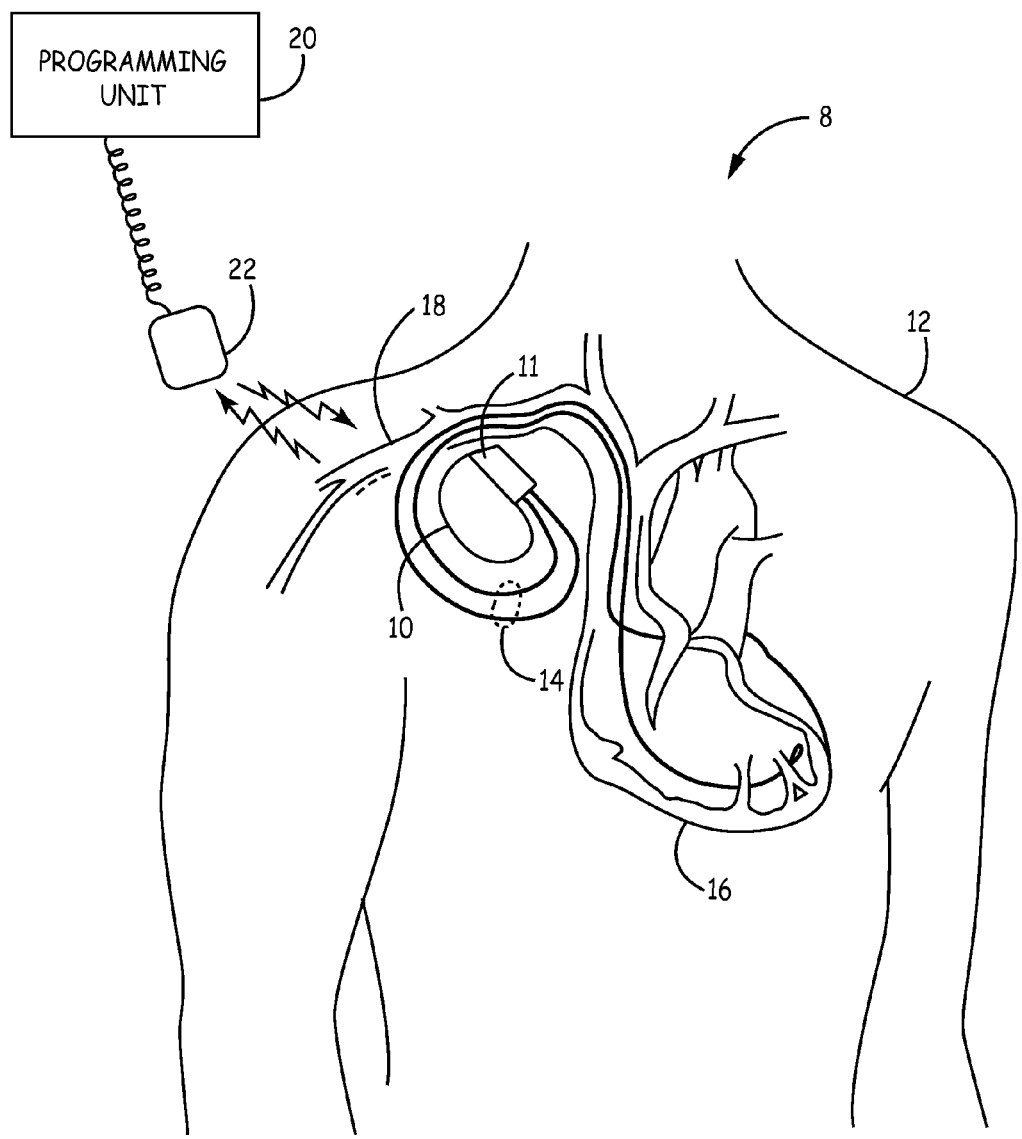
FIG. 1 illustrates an exemplary implantable medical system.

FIG. 1 illustrates an implantable medical system 8, which includes, for example, an implantable medical device ("IMD") 10 that has been implanted in a patient 12. The IMD 10 is housed within a hermetically sealed, biologically inert outer canister or housing, which may itself be conductive so as to serve as an electrode in the pacing/sensing circuit. One or more leads, collectively identified with reference numeral 14 are electrically coupled to the IMD 10 in a conventional manner and extend into the patient's heart 16 via a vein 18. Disposed generally near a distal end of the leads 14 are one or more conductive electrodes for receiving electrical cardiac signals or delivering electrical pacing stimuli to the heart 16. The leads 14 may be implanted with their distal end situated in either the atrium or ventricle of the heart 16.

Although the disclosure is described herein in an embodiment that includes a cardiac device, it may be advantageously embodied in numerous other types of implantable medical systems in which it is desirable to optimize the energy consumption of an implanted device with a finite energy source.

With continued reference to FIG. 1, an external programming unit 20 is depicted for non-invasive communication with the IMD 10 via conventional uplink and downlink communication channels, which are not described in greater detail herein so as to avoid unnecessarily obscuring the details of the present disclosure. In an embodiment, the programming unit 20 may be associated with a programming head 22, in accordance with conventional medical device programming systems, for facilitating two-way communication between the IMD 10 and the programmer 20. In many known implantable systems, the programming head 22, such as that depicted in FIG. 1, is positioned on the patient's body over the implant site of the device 10 (usually within about 2 to about 3 inches, or equivalently, about 5 to about 8 cm, of skin contact), such that one or more antennas within the head 22 can send radio frequency (RF) signals to, and receive radio frequency (RF) signals from, an antenna (not shown) disposed within the hermetic enclosure of the implanted device 110 or disposed within a connector block 11 of the device 10, in accordance with common practice in the art.

Figure 2:
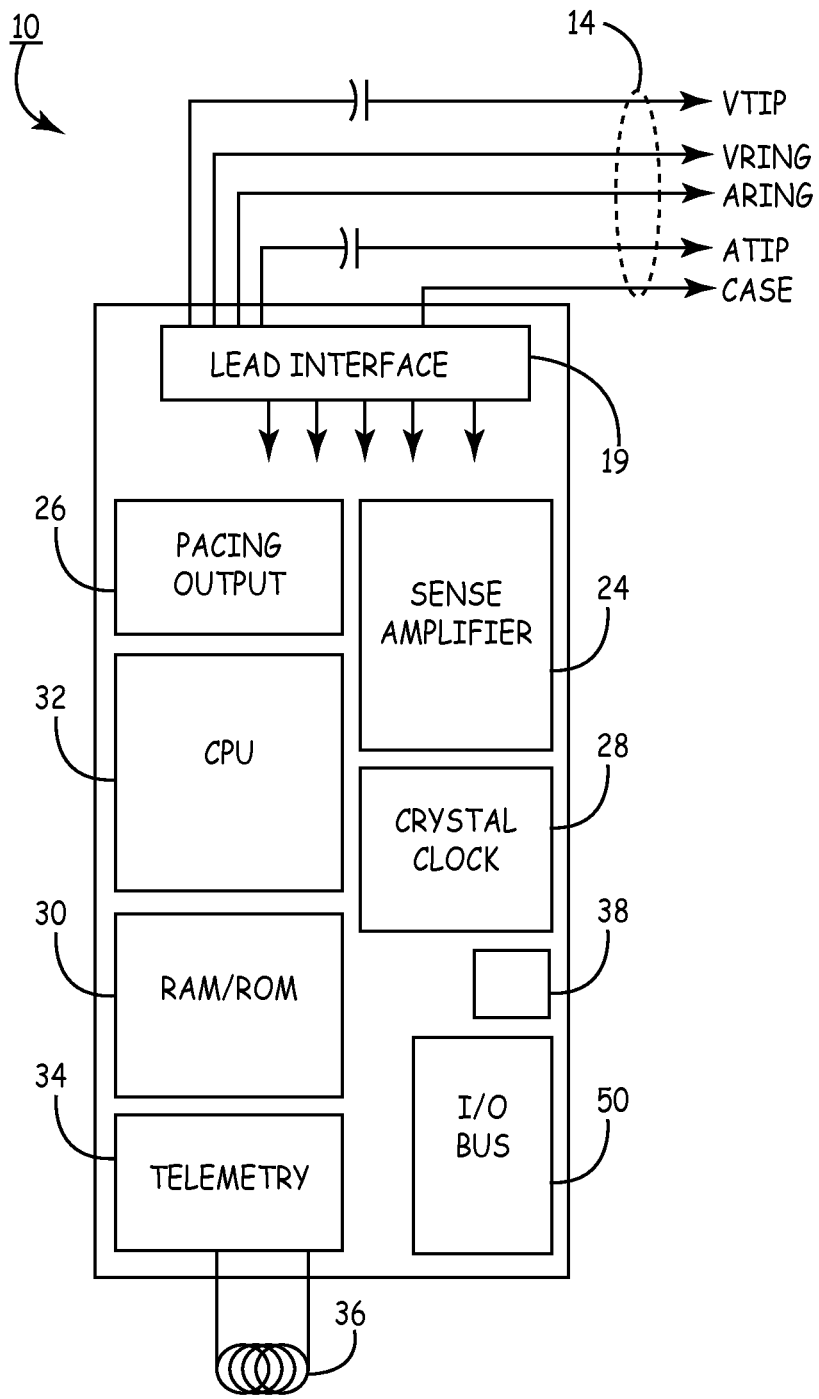
FIG. 2 depicts a block diagram of one exemplary embodiment of electronic circuitry for an implantable medical device (IMD)

FIG. 2 provides a general block diagram of electronic circuitry that makes up the IMD 10. The IMD 10 is a device capable of performing a variety of functions, such as delivering electrical stimulation therapy to the patient 12 in accordance with the presently disclosed embodiment of the disclosure. FIG. 2 shows that IMD 10 comprises circuitry for controlling the device's pacing and sensing functions. Aspects of the IMD circuitry may be of conventional design, in accordance for example, with what is disclosed in U.S. Pat. No. 5,052,388 issued to Sivula et al. and entitled "Method and Apparatus for Implementing Activity Sensing in a Pulse Generator." The '388 patent is hereby incorporated by reference herein in its entirety.

To the extent that certain components of the circuitry of the IMD 10 are conventional in their design and operation, such components will not be described herein in detail because it is believed that design and implementation of such components would be a matter of routine practice to those of ordinary skill in the art. For example, the circuitry of the IMD 10 shown in FIG. 2 includes sense amplifier circuitry 24, stimulating pulse output circuitry 26, a crystal clock 28, a random-access memory and read-only memory (RAM/ROM) unit 30, and a pacing timing and control circuit in the form of a programmed control unit 32. The control unit 32 may be a digital signal processing component such as a microprocessor or a microcontroller. While the embodiment of FIG. 2 refers to a digital signal processor-based architecture, it should be noted that other architectures, such as the logic or state machine architectures or other components or circuitry for performing a processing function, are contemplated in the present disclosure. Such architectures are not discussed in detail herein merely for the sake of brevity.

The IMD 10 also includes an internal telemetry communications circuit 34 coupled to an antenna 36 so that it is capable of communicating with the external programmer/control unit 20. Various telemetry systems for providing the uplink and downlink communication channels between the external programming unit 20 and the IMD 10 have been shown in the art and may be employed herein without departing from the spirit and scope of the disclosure.

With continued reference to FIG. 2, the IMD 10 is coupled to one or more leads 14 which, when implanted, extend transvenously between the implant site of the IMD 10 and the patient's heart 16, as previously noted with reference to FIG.

1. Physically, the connections between the leads 14 and the various internal components of the IMD 10 are facilitated by a conventional connector block assembly 11, shown in FIG. 1. Electrically, the coupling of the leads 14 and the internal electrical components of the IMD 10 may be facilitated by a lead interface circuit 19, which functions, in a multiplexer-like manner, to selectively and dynamically establish necessary connections between various conductors in the leads 14, including, for example, atrial tip and ring electrode conductors ATIP and ARING and ventricular tip and ring electrode conductors VTIP and VRING, and individual electrical components of the IMD 10, as would be familiar to those of ordinary skill in the art. For the sake of clarity, the specific connections between the leads 14 and the various components of the IMD 10 are not shown in FIG. 2, although it will be clear to those of ordinary skill in the art that, for example, the leads 14 will necessarily be coupled, either directly or indirectly, to sense amplifier circuitry 24 and stimulating pulse output circuitry 26, in accordance with common practice, such that cardiac electrical signals may be conveyed to the sense amplifier circuitry 24, and such that stimulating pulses may be delivered to cardiac tissue, via the leads 14.

It will be appreciated that the signals received over the leads 14 by the sense amplifier circuitry 24 may be collected and stored in the RAM/ROM unit 30 by the control unit 32 acting under control of software also stored in the RAM/ROM unit 30. Additional data, such as the timing of signals delivered by the stimulating pulse output circuitry 26 may also be stored in the RAM/ROM unit 30. This stored data may be later retrieved and delivered to the programming unit 20 via the telemetry communications circuit 34.

As previously noted, the circuitry of the IMD 10 includes the control unit 32 which may be an off-the-shelf programmable microprocessor or microcontroller, but in the presently illustrated embodiment of the disclosure is a custom integrated circuit. Although specific connections between the control unit 32 and other components of the IMD circuitry are not shown in FIG. 2, it will be apparent to those of ordinary skill in the art that the control unit 32 functions to control the timed operation of the stimulating pulse output circuit 26 and the sense amplifier circuit 24 under control of a program of instructions stored in the RAM/ROM unit 30.

In one embodiment, clock 28 in the presently illustrated embodiment is a crystal controlled oscillator that provides a main timing clock signal ($F_0$). In another embodiment, the clock 28 may include a clock generator such as a crystal oscillator for providing a first clock signal of one frequency ($F_0$) and a programmable frequency divider for generating multiple clock signals of different frequencies from the first clock signal and for outputting one of the multiple clock signals ($F_1$-$F_n$). Again, the lines over which the aforementioned clock signals are provided to the various components of the IMD 10 (e.g., the control unit 32) are omitted from FIG. 2 for the sake of clarity. It is believed that those of ordinary skill in the art will be familiar with such an operative arrangement.

It is to be understood that the various components of the IMD 10 depicted in FIG. 2 are powered by means of a battery 38, which is contained within the hermetic enclosure of the IMD 10, in accordance with common practice in the art. For the sake of clarity in the drawings, the connections between the battery and the other components of the IMD 10 are not shown.

Those of ordinary skill in the art will appreciate that the IMD 10 may include numerous other components and subsystems, for example, activity sensors and associated circuitry. The presence or absence of such additional components in the IMD 10, however, is not believed to be directly pertinent to the disclosure, which relates generally to optimizing operation of the microcontroller to minimize power consumption and promote an extension of the life of the energy source.

Stimulating pulse output circuitry 26, which functions to generate cardiac stimuli under control of signals issued by the control unit 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits, which would be suitable for the purposes of practicing the disclosure. The sense amplifier circuitry 24, may be, for example, of the type disclosed in U.S. Pat. No. 4,357,943 to Thompson, entitled "Demand Cardiac Pacemaker Having Reduced Polarity Disparity," which patent is hereby incorporated by reference herein in its entirety.

Generally, the sense amplifier circuitry 24 functions to receive electrical cardiac signals from the leads 14 and to process such signals to derive event signals reflecting the occurrence of specific cardiac electrical events, including atrial contractions (P-waves) and ventricular contractions (R-waves). These event-indicating signals are provided to the control unit 32 for use by the control unit 32 in controlling the synchronous stimulating operations of the IMD 10 in accordance with common practice in the art. In addition, these event-indicating signals, as discussed above, may be communicated, via the uplink communication channel, to the external programming unit 20 for storage and visual display to a physician or clinician.

It is important to note that leadless embodiments of the present disclosure are also contemplated, where one or more stimulation and/or sensing electrode capsules or modules are implanted at or near a desired target tissue site, and the capsules or modules deliver electrical stimuli directly to the site using a preprogrammed stimulation regime, and/or the capsules or modules sense electrical or other pertinent signals.

In addition to the sensed physiologic events, it is contemplated that additional activities will give rise to a need for signal processing. As such, "events" as used in the present disclosure refer to activities, data handling requests, or other activity that result in a need for a processing function being performed by the control unit 32. Examples of such events include an intrinsic sense signal, a pacing pulse, noise interference, and numerous other activities, any of which result in a processing action to be performed by the control unit 32.

In conventional IMDs, the operation of the control unit typically requires several times more operating power than other circuitry and components in the IMD. The events that trigger the sensing or generation of the event signals to be provided to the control unit 32 to be processed generally occur frequently but in an irregular manner. Moreover, each individual event signal is generated at a point in time substantially corresponding with the occurrence of the event. This operation causes the event signals to also be provided in a correspondingly frequent and irregular manner (individually) to the control unit 32 for processing. A further implication of the operation of this conventional operation is that the control unit needs to be almost perpetually in a wake up state so as to receive the frequent but irregularly occurring events for processing.

However, the inventors of the present disclosure have observed that maintaining the control unit 32 in the wake up state for receipt and processing of each individual event results in inefficiencies in the power consumption. This is because the control unit needs to be powered on (or the power supply sustained) to enable appropriate handling and response to the occurrence of each event. As such, the present disclosure describes techniques to optimize the operations of the control unit and minimize power consumption.

Figure 3:
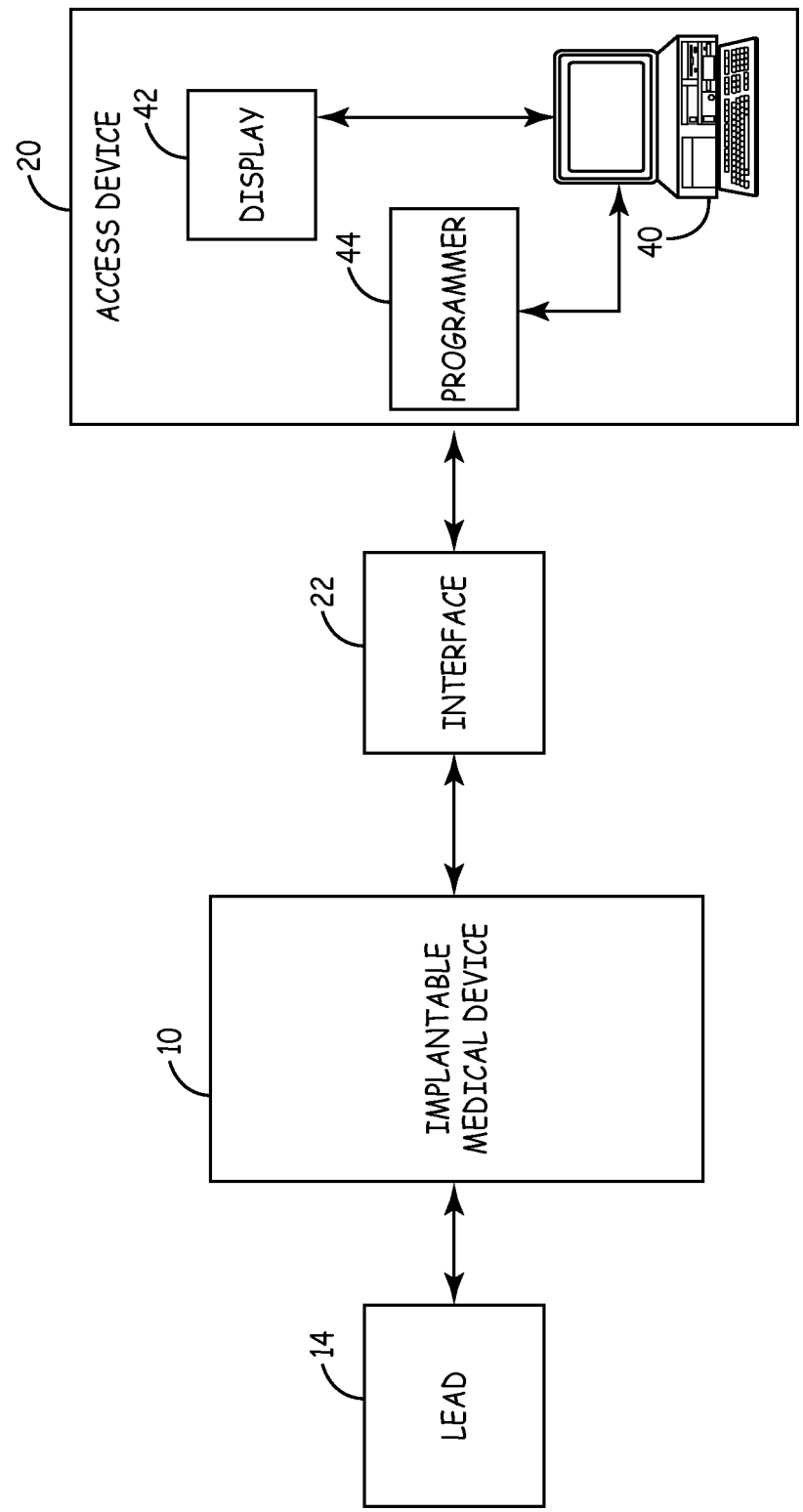
FIG. 3 illustrates an external programmer associated with the IMD.

FIG. 3 illustrates a more detailed illustration of the external programmer/control unit 20. In one embodiment, the programmer/control unit 20 comprises a computer system 40, a display device 42, and a processing unit 44. In one embodiment, the processing unit 44 can be integrated into the computer system 40. The computer system 40 can prompt the acquisition of physiologic data from the cardiac IMD 10 via the programming head 22. The computer system 40 can then display the physiologic data on the display device 42. The display device 42 can display physiologic data from the reference point of different time periods, different activity results, and the like.

Figure 4:
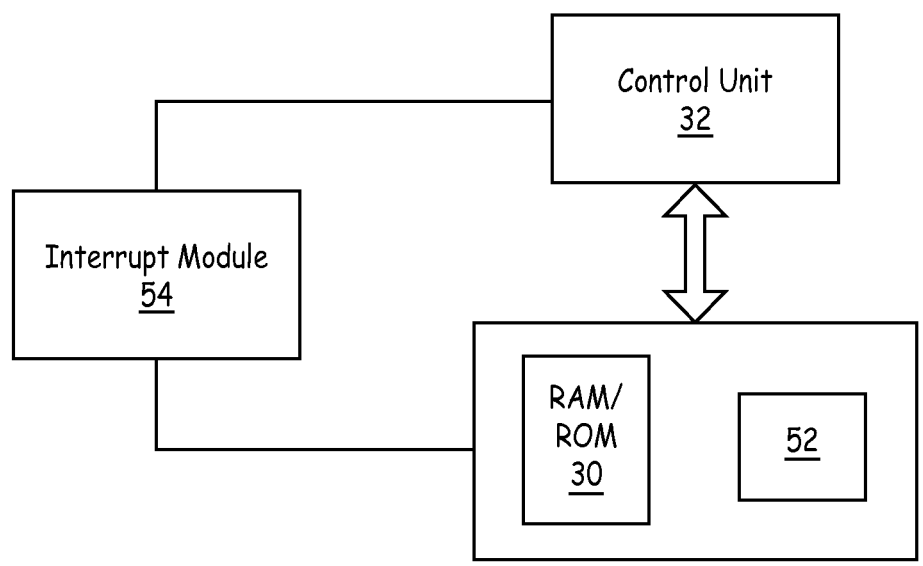
FIG. 4 illustrates a block diagram of one embodiment of an IMD.

Turning now to FIG. 4, a more detailed block diagram of one embodiment of the IMD 10 is illustrated. Numerous components of IMD 10 known to those skilled in the art have been omitted for the sake of brevity. The block diagram depicts one embodiment of implementing a digital signal processor-based power saving technique in an implantable medical device in accordance with the present disclosure. The control unit 32 performs tasks that are dictated by instructions that are stored within the IMD 10. The instructions, which comprise programs for execution by the control unit 32, may be stored in the RAM/ROM unit 30. The control unit 32 acquires the instructions from the RAM/ROM unit 30 via the bus 50. In an alternative embodiment, the instructions may be stored in a non-volatile memory 52. In one embodiment, the non-volatile memory 52 may comprise an EEPROM, a PROM, a flash memory unit, and/or other non-volatile memory devices.

In one embodiment, the IMD 10 may include an interrupt module 54 that is coupled to the control unit 32. The interrupt module 54 provides data and control signals associated with events to be processed by the control unit 32. In one implementation, the control signals issued by the interrupt module 54 include an indication that alerts the control unit 32 that events are available to be processed. Control unit 32 performs processing operations of the event data in response to receiving the control signals rather than handling the events in the ad hoc nature in which they arise. The interrupt module 54 further controls the supply of power to the control unit 32 so as to ensure that an appropriate amount of power is provided to the control unit 32 for processing of the event data associated with the received events. As such, the control signals issued by interrupt module 54 provides an indication to the control unit 32 that one or more events that are available for processing.

The interrupt module 54 may be programmed to control the number and nature of events that are stored prior to issuing the control signal to alert and provide the event data to the control unit 32. In addition, the duration between the actual occurrence of each individual event and the issuance of the control signal may be programmed. The duration may be dependent on the type and nature of the event such that in one instance time critical events are processed in a timely manner and non-critical events are processed in batch, for example. The number of events that are stored and the frequency of providing the stored event data to the control unit 32 may also be predefined based upon one or more factors. For instance, critical events may trigger issuance of an immediate alert to initiate processing while other events, such as non-therapy dependent events may be stored and an alert issued to trigger transfer of the data on a predefined regular interval such, for example, as every other hour, twice a day, once a week or any other one or more predefined interval.

The interrupt module 54 may function in conjunction with other circuitry in the IMD 10 to initiate the processing of events. For example, an event queue (shown in FIGS. 5 and 6) may be utilized for storage of the events. The instructions to be executed when the events are received may be stored in a memory unit such as the RAM/ROM unit 30 and delivered via the bus 50. It is also contemplated that one or more of the memory units may be utilized for storage of the events as they are received.

An additional, optional, aspect of the embodiments may involve regulating a clock signal provided to control unit 32 based on the control signals issued by interrupt module 54. In one implementation, the control unit 32 includes a clock (not shown) that generates a high frequency signal during or contemporaneously with initiation of the wake up state but otherwise remains turned off during the idle state. As such, the control unit clock will draw sufficient power from the battery during the wake up state to generate the high frequency clock although the frequency and duration of generating the high frequency clock—and hence the power drain—is regulated by the issuance of the control signals. Thus, significant power savings can be realized by only generating the high frequency signal responsive to the interrupt signal and during the idle state, while holding the power consumption to the bare minimal leakage current drain that may be exhibited by the clock.

Although not shown in the drawings for the sake of brevity, it is further contemplated that various embodiments of the disclosure may utilize multiple clock signals generated by separate clocks, in conjunction with, or solely by the aforementioned clock 28, for example. The multiple clock signals may, for example, include a stream-bus clock signal and a reference clock signal. In that example, a low frequency signal may be generated by the reference clock with the low frequency clock signal being utilized by various IMD components to facilitate the reception of events or during the idle state. Further, in the example, a stream-bus clock may generate a low frequency stream-bus clock signal that is utilized by the IMD circuitry for transmission of the received event data to the event queue. The generation of these multiple clock signals may further be controlled by the interrupt module 54 as a function of the receipt of events, transfer of the event data among the IMD components and processing of the event data. In other embodiments, it is contemplated that the control unit may further receive a lower frequency clock signal (in relation to the high frequency signal) such as that generated by the reference clock, during for example the idle state.

Managing the receipt and prioritization of the events in the interrupt module 54, as described in this disclosure, eliminates the requirement in conventional IMDs to process each of the events as it is received. The conventional manner of handling and processing the events also requires the control units to be powered as each event is received so that the data associated with the events can be processed. The present disclosure obviates the need to power the control unit 32 with each event occurrence. By providing power to the control unit 32 in a systematic predetermined fashion, as a function of the events to be processed, substantial power savings are achieved. Further, providing the high frequency clock signal to the control unit only during times when event data is being processed eliminates undue power drain that is otherwise associated with unnecessarily generating the high frequency clock signal at all times. As such, the present disclosure enables the user to define specific use parameters and integrate any necessary design constraints for a more accurate forecast of the power consumption.

In one implementation, the supply of power to the control unit 32 is controlled at least partially based on the communications from the interrupt module 54. For example, in response to criteria being met for the interrupt module 54 to provide events to the control unit 32 for processing, the control unit 32 may transition from a first state to a second state. The first and second state may be an idle state and a wake up state, respectively, in one embodiment.

In the idle state the control unit 32 is provided with power at a "first power level" in which the control unit 32 essentially consumes little to no current. The idle state corresponds to a duration in which control unit 32 is not executing instructions or processing data associated with events and because no processing function is being performed, little or no power needs to be provided to the control unit 32. The wake up state corresponds to the duration during which the control unit 32 consumes a "second power level" corresponding to a normal power level as defined by its respective manufacturer's operating conditions. In other words, the interrupt module 54 provides a control signal to the power source indicating that the control unit 32 should be switched to the wake up state in response to criteria for transmitting the events to the control unit 32 being met. Consequently, the control unit 32 is supplied with an appropriate power level as well as data for which a requested operation is to be performed so as to provide among other things the logic decisions for operating the IMD 10.

The criteria by which the interrupt module transmits event data to the control unit 32 may comprise synchronous or asynchronously timed transfers. For example, the criteria may include storing event data associated with the events that have occurred during a time window (defined by a pre-specified time interval) and providing the event data upon expiration of the time window. An alternate criterion may include storing a predetermined number of events and providing those stored events to the control unit 32 in response to the number of events matching the predetermined limit. Another criterion may include grouping or classifying events as they occur into a plurality of categories each category having a priority allocation and storing the events to be subsequently provided to the control unit 32 based on the priority allocation. The priority allocation may signify events that are to be provided to the control unit 32 immediately, or within a given duration and/or that a predetermined number of events is to be stored and provided to the control unit 32 once the predetermined limit is reached and/or that all events or events in a given category are to be provided to the control unit 32 based upon passage of a pre-specified duration.

Figure 5:
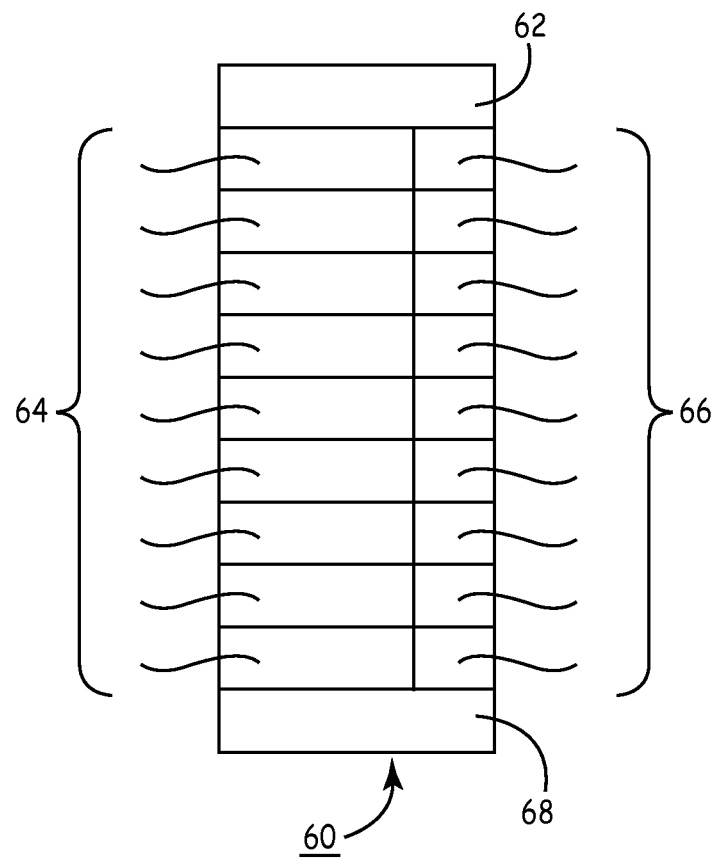
FIGS. 5 and 6 depict alternative embodiments of an event queue.
Figure 6:
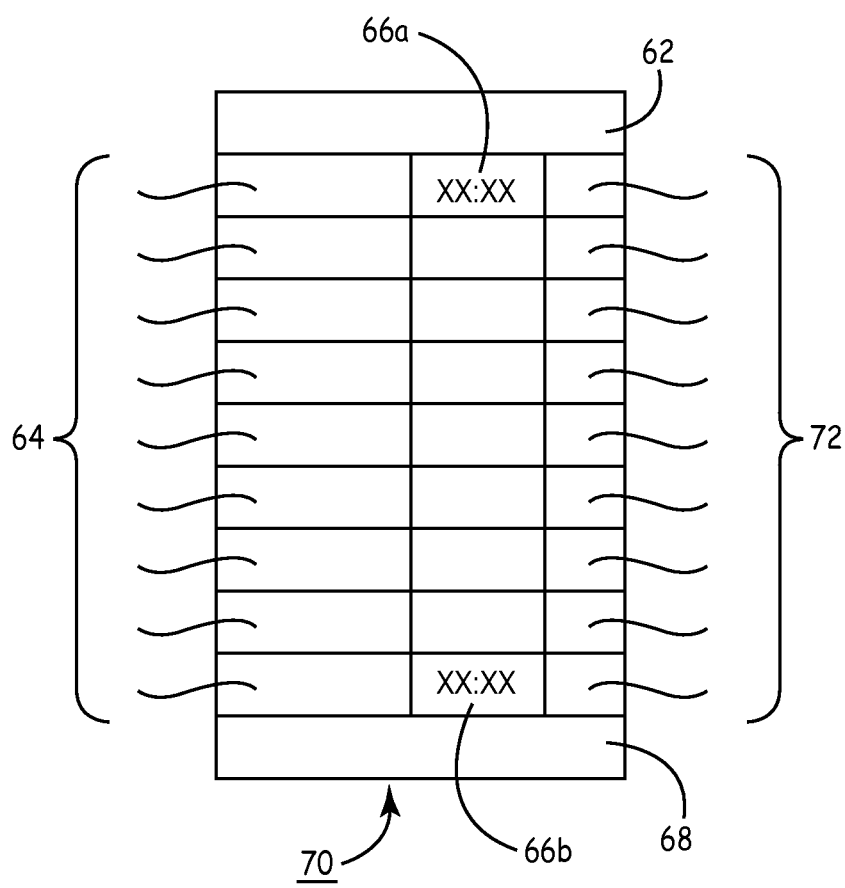

FIGS. 5 and 6 depict alternative embodiments of an event queue. The event queue may be embodied in hardware, software, firmware or a combination of any two or all three. In accordance with the present disclosure, the event queue is provided to facilitate the control of processing of events by a control unit. In doing so, power consumption by the control unit can be optimized. Turning to FIG. 5, an event queue 60 may include a head pointer 62, a plurality of data segments 64, (optionally) a plurality of timestamps 66 each of which may correspond to the time of receipt of an associated one of the plurality of data segments 64, and a tail pointer 68. The event queue 60 may have a variable length which is to say that the plurality of data segments 64 may vary from one event queue 60 to another based on the criteria employed. In other words, the number of individual data segments 64, each of which corresponds to a location for storage of an individual event, may be defined by a predetermined number of events. In some embodiments, each of the data segments 64 may be individually addressable to permit various access schemes of the event data such as first-in first-out, or first-in last-out, or retrieval based on a priority classification, or some other data access scheme. The head pointer tracks the events stored by hardware, and the tail pointer will track the events provided to the control unit 32.

In one embodiment, upon receiving an event, the interrupt module 54 stores the event in one of the data segments 64 of the event queue 60. The events may be stored sequentially, randomly, or in any other desired arrangement. For example, in the first-in first-out scheme, the tail pointer 68 may be moved to the top of the segment stack upon providing the data in the event queue to the control unit 32 for processing. In that example, the head pointer 62 is positioned adjacent to the segment immediately following the tail pointer 68 to indicate it as the first available segment for event storage. Upon storing an event in the first available segment, the head pointer 62 is moved to the next available segment and so forth. As the event is detected and stored, the interrupt module will store the pertinent event information in the data segments. The storing of the events in the event queue 60 enables management of the flow of events to the control unit 32. The use of the event queue 60 modulates the frequency with which the control unit 32 is powered as a result of processing requests associated with the events.

In an alternative embodiment, each event queue may be time-stamped and maintained in the event queue 60 in the selected order. The time-stamp may suitably be applied to each event in yet another embodiment.

The interrupt module 54 is programmed in accordance with criteria corresponding to any one or more of the above discussed criteria to generate a control signal to manage the power supply to the control unit 32 and provide the events in event queue 60 to the control unit 32 for processing. For example, the interrupt module 54 will be programmed to generate the control signal after the number of events in the event queue matches the predetermined number of events, in one embodiment. In other words, in response to the number of events between tail pointer 62 and head pointer 68 matching the predetermined number, an interrupt occurs and the firmware executes to gather the event information, and reprograms the location of the tail pointer. This power-saving technique provides the flexibility to control how frequently the control unit 32 starts and stops running based on the availability of event information.

FIG. 6 depicts another embodiment of an event queue. Event queue 70 may include a head pointer 62, a plurality of data segments 64, a plurality of optional timestamps 66, a tail pointer 68, and an optional classification code 72. The elements of event queue 70 corresponding to those of event queue 60, in the embodiment of FIG. 5, are numbered with identical reference designators. The reader is referred to the preceding description of FIG. 5 for a full discussion pertaining to those components.

In the illustration, the size of each discrete event queue to be acted upon by the control unit 32 is based upon a time interval. As such, the timestamps 66 may be utilized to determine the events that occurred within a given duration. In an alternative embodiment, the timestamps 66a, 66b may be associated with a first event in a given queue and a last event in the given queue with all events occurring between the first and last event being handled together. In another embodiment, the first event is timestamped when it is stored in the event queue 60 with the subsequent events being written in a first-in, first-out manner and accessed via the same. The last event is also timestamped to indicate the address of the last event in that given queue. Thus the event in the first data segment will be the first event read out to the control unit 32 and the event in the second data segment will be the second event read, and so on and so forth until the last event is read.

In an alternative embodiment, the classification code 72 identifies categories of events and the codes associated with each category may be used to prioritize the reading of events in a given queue or in multiple queues. For example, a first code may be associated with intrinsic sensed signals, a second code associated with pacing pulse signals, and a third code associated with noise interference. In the example, priority of reading the event data may be as follows: the events tagged with the first code are read and provided to the control unit 32 within five (5) microseconds of its occurrence, the events tagged with the second code and third code are read and provided to the control unit 32 in a first-in, first-out format, except that all the events tagged with the second code are read and provided before the events tagged with the third code.

In yet another embodiment, the timestamps 66 and classification code 72 may be utilized together such that the classification code denotes the overall order in which the events are read, and the timestamps 66 determines the sequence in which events within each given classification code 72 are read.

The interrupt module 54 may be synchronized to a predetermined duration that corresponds to a wake up interval of the control unit 32. In such an implementation, the interrupt module 54 provides the event information stored in the event queue corresponding to the predetermined duration (as a function of the time-stamps). This may be performed irrespective of the number of events that were stored during the corresponding time interval.

Figure 7:
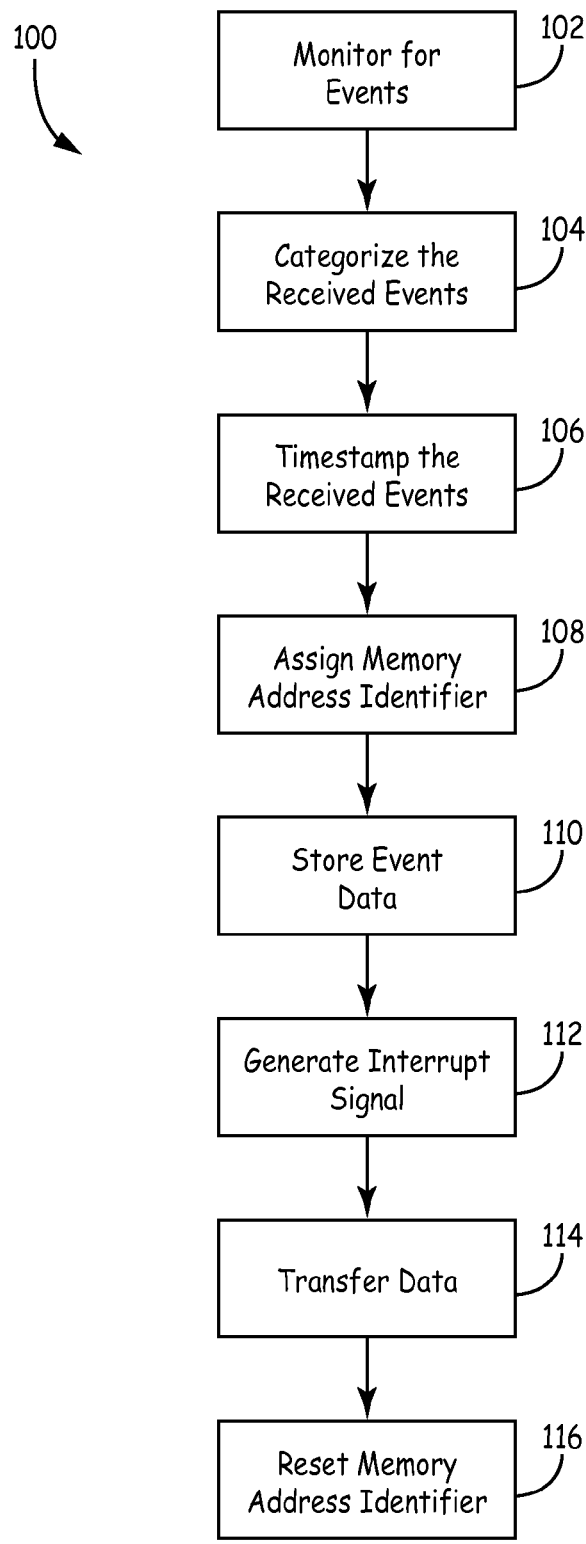
FIG. 7 illustrates a method for acquisition and storage in an event queue of data associated with an event.

FIG. 7 illustrates a method 100 for event data acquisition. The order in which the method is described is not intended to be construed as a limitation, and any number of the described method blocks can be combined in any order to implement the method. Furthermore, the method can be implemented in any suitable hardware, software, firmware, or combination thereof.

At block 102, events are received from various sources including internal components, external components, and other devices communicatively-coupled to IMD 10. For example, interrupt module 54 may receive event data from a memory location in RAM/ROM 30, a sensor on the IMD lead, or the external programmer. The received data may optionally be categorized at block (104) and subsequently may optionally be time-stamped (106). For the categorization, the event data may be labeled, or otherwise identified, with a source identifier corresponding to the source of each data segment. In one example, data received from the sensor may be categorized as ES, while event data received from the programmer may be categorized under EP. A timestamp such as "time1", representing a first time window, or a specific time derived from a clock may be applied for each event.

Further, the event data is identified with a memory address identifier corresponding to a memory address of the event queue at block (108). A memory address identifies the data segment as having either header information (head pointer 62), event information (the plurality of data segments 64), or the tail information (tail pointer 68). At block 110, the event information is written into one of the plurality of data segments 68 in the predefined data format. At block (112), an interrupt signal is generated in response to a given criteria being met. For example, the interrupt signal is generated in response to the first-in, first-out memory component exceeding a threshold number of stored data segments. As another example, the interrupt signal is generated in response to a predetermined duration being met.

At block (114), the event information in the plurality of data segments 64 is read out/transferred to the processor. In response to determining that all the data segments in the event queue have been read, the memory address identifiers and optionally the tail pointer 68 and head pointer 62 may be reset (116).

Figure 8:
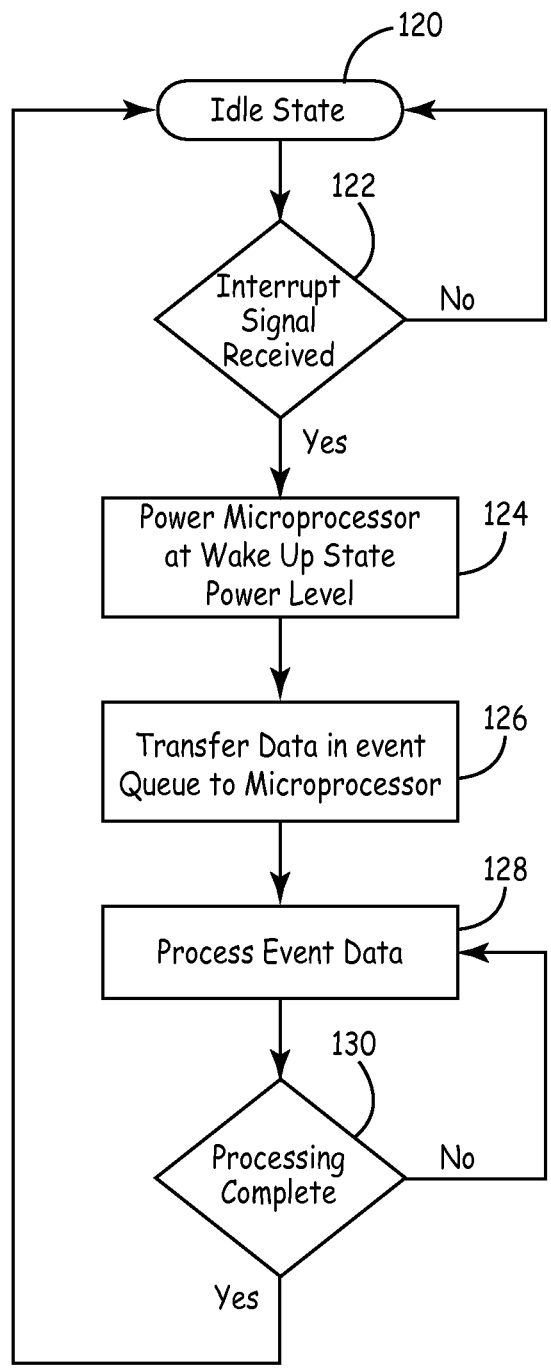
FIG. 8 depicts a flow chart describing the steps of utilizing an event queue.

Referring now to FIG. 8, a flow chart is provided for describing the steps of utilizing an event queue to optimize the operation of a control unit to minimize power consumption. The flow chart commences, in the initial step (120), assuming that the control unit 22 is not executing any code nor processing any events that may have been previously provided. This state may correspond to the aforementioned idle state and the control unit 22 remains in this state until a control signal is received. The interrupt module 54 may issue a control signal which is received by the control unit 22 (block 122). Concurrently or subsequent to receiving the control signal, the power source of the IMD 10 is regulated to appropriately power the control unit 22 (block 124). The transmission of power at block 122 places the control unit 22 in a wake up state. In some embodiments, the power supply may be regulated to provide varying power levels where the variation may depend, for example, on the classification of event or the event information available in the event queue to be processed. As noted with respect to the description in FIGS. 5 and 6, the interrupt module 54 will transmit the event information stored in the event queue to the control unit 22. At block (126), the control unit 22 reads the event data in each of the data segments 64 in the event queue for transfer to the processor. The data is received by the processor and the processor performs the required processing function (block 128). The read operation is performed for each data segment until all events have been read (block 130). In response to determining the completion of the reading and processing of event information for each data segment in the event queue, the control unit 22 returns to the idle state to facilitate conservation of power.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

What is claimed is:

1. An implantable medical device having at least one integrated circuit comprising:
   a memory comprising for storing event data associated with one or more received events;
   a control unit comprising for processing the event data;
   an interrupt module comprising for controlling transfer of the event data to the control unit; and
   a power supply comprising for delivering power to the control unit at a first power level and a second power level, wherein one of the first power level and the second power level are delivered in response to a control signal generated by the interrupt module, and
   wherein the interrupt module is configured to generate the control signal for controlling the delivery of the first power level and the second power level and the generating of the control signal is triggered by transfer of the event data.

2. The implantable medical device of claim 1, wherein the memory comprises an event queue.

3. The implantable medical device of claim 1, wherein the interrupt module generates the control signal based on predetermined criteria.

4. The implantable medical device of claim 3, wherein the predetermined criteria is selected from the group consisting of a duration, a classification of received events, and a storage of predefined number of events.

5. The implantable medical device of claim 1, wherein the first power level corresponds to an idle state power level.

6. The implantable medical device of claim 1, wherein the event data includes a classification of a received event.

7. The implantable medical device of claim 1, wherein the event data includes a timestamp indicating a time of receipt of an event.

8. The implantable medical device of claim 1, further comprising one or more clocks for generating a plurality of clock signals, wherein one of the plurality of clock signals is output to the control unit based on the control signal.

9. The implantable medical device of claim 8, wherein the plurality of clock signals includes a high frequency clock signal and a reference clock signal that is slower than the high frequency clock signal, and wherein the reference clock signal being output to the control unit during an idle state power level.

* * * * *